US012637742B2

(12) United States Patent
Edick et al.

(10) Patent No.: US 12,637,742 B2
(45) Date of Patent: May 26, 2026

(54) BIOABSORBABLE MAGNESIUM ALLOY FOR IMPLANTS WITH ENGINEERED ABSORPTION

(71) Applicant: Magsorbeo Biomedical Corp., Detroit, MI (US)

(72) Inventors: Jacob Drew Edick, Rochester, MI (US); Carolyn Joan Lahti Woldring, Rochester, MI (US)

(73) Assignee: Magsorbeo Biomedical Corp., Detroit, MI (US)

( * ) Notice: Subject to any disclaimer, the term of this patent is extended or adjusted under 35 U.S.C. 154(b) by 287 days.

(21) Appl. No.: 18/121,976

(22) Filed: Mar. 15, 2023

(65) Prior Publication Data

US 2024/0043969 A1 Feb. 8, 2024

Related U.S. Application Data

(60) Provisional application No. 63/319,898, filed on Mar. 15, 2022.

(51) Int. Cl.
*C22C 23/04* (2006.01)
*A61L 31/02* (2006.01)
*A61L 31/14* (2006.01)

(52) U.S. Cl.
CPC ............ *C22C 23/04* (2013.01); *A61L 31/022* (2013.01); *A61L 31/148* (2013.01)

(58) Field of Classification Search
CPC .................................. C22C 23/04; C22F 1/06
See application file for complete search history.

(56) References Cited

U.S. PATENT DOCUMENTS

| | | | |
|---|---|---|---|
| 9,469,889 B2 | 10/2016 | Imwinkelried | |
| 9,593,397 B2 | 3/2017 | Imwinkelried | |
| 9,757,174 B2 | 9/2017 | Weinberg | |
| 9,943,625 B2 | 4/2018 | Koo | |
| 10,024,470 B2 | 7/2018 | Decker | |
| 10,196,715 B2 | 2/2019 | Imwinkelried | |
| 10,266,922 B2 | 4/2019 | Manuel | |
| 10,344,365 B2 | 7/2019 | Mueller | |
| 10,358,709 B2 | 7/2019 | Mueller | |
| 10,478,529 B2 | 11/2019 | Imwinkelried | |
| 2019/0249286 A1 | 8/2019 | Kim | |
| 2019/0284670 A1 | 9/2019 | Mueller | |
| 2020/0123636 A1 | 4/2020 | Eliezer | |
| 2020/0384160 A1 | 12/2020 | Decker | |

OTHER PUBLICATIONS

Bakhsheshi-Rad, H. R., et al. "Mechanical and bio-corrosion properties of quaternary Mg—Ca—Mn—Zn alloys compared with binary Mg—Ca alloys." Materials & Design 53 (2014): 283-292.*

* cited by examiner

*Primary Examiner* — Jessee R Roe
(74) *Attorney, Agent, or Firm* — Christensen, Fonder, Dardi & Busse PLLC Timothy J. Busse

(57) ABSTRACT

The present disclosure generally relates to a magnesium alloy including about 2-7% by weight zinc; about 0.2-3% by weight calcium; about 0-1.0% by weight of an alloying element; and a balance of magnesium. The magnesium alloy may include a ternary absorption profile including a first absorption rate, second absorption rate, and third absorption rate, the second absorption rate being approximately slower than the first absorption rate and the third absorption rate. The magnesium alloy may be formed as a portion or more of a bodily implant.

11 Claims, 1 Drawing Sheet

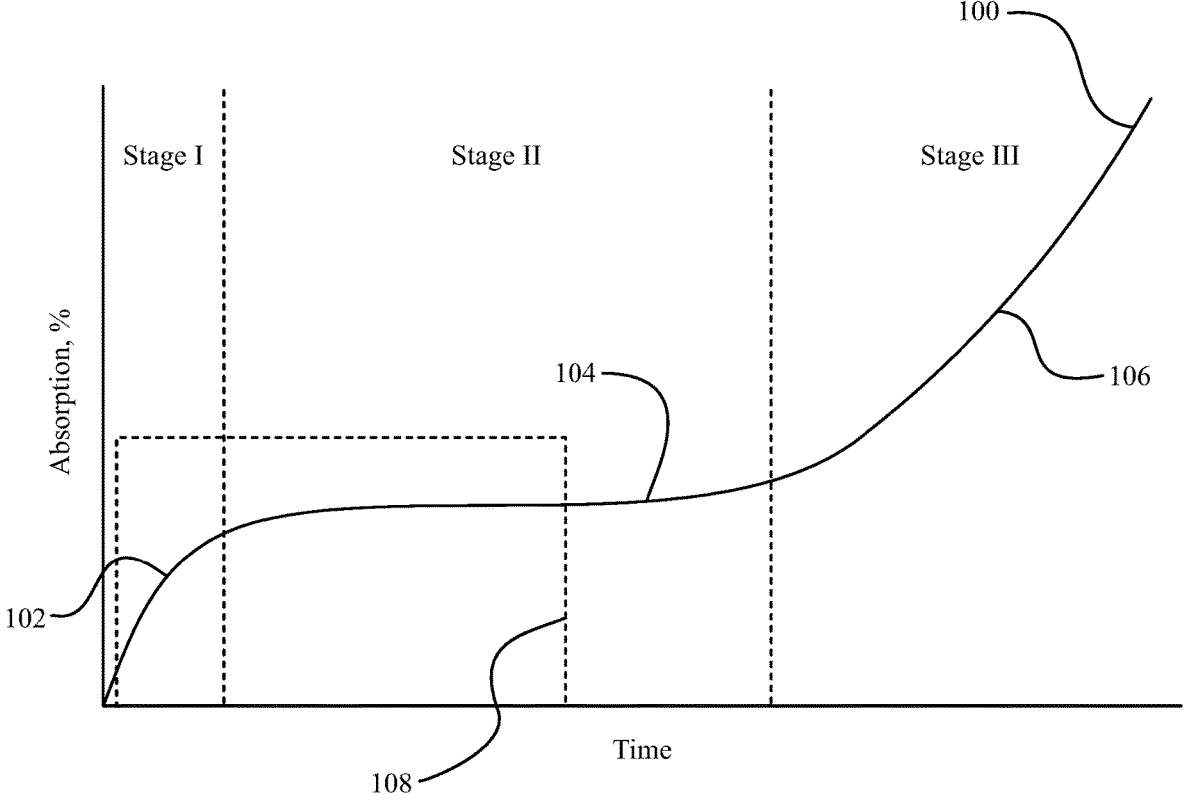

BIOABSORBABLE MAGNESIUM ALLOY FOR IMPLANTS WITH ENGINEERED ABSORPTION

CROSS-REFERENCE TO RELATED APPLICATIONS

This application claims the benefit of U.S. Provisional Application No. 63/319,898 filed Mar. 15, 2022.

TECHNICAL FIELD

The disclosed embodiments generally relate to magnesium alloys.

BACKGROUND

Magnesium alloys are effective for use in temporary medical devices, such as temporary implants. However, typical magnesium alloys may include material or mechanical characteristics that degrade too quickly or too slowly over time and do not have absorption profiles that meet the needs of particular applications.

Magnesium alloy-based temporary implants lasting longer than two years, and occasionally as low as one year, do not achieve the benefits of absorption which may be a desired performance characteristic of a temporary implant. Alternatively, magnesium alloy-based temporary implants that degrade too fast will not be able to meet the mechanical needs to promote safe and effective healing of an implant recipient. Therefore, a bioabsorbable magnesium alloy with an absorption profile suitable to match the needs of varying applications and absorb safely over the desired timeframe is needed.

SUMMARY OF THE INVENTION

This summary is provided to introduce a variety of concepts in a simplified form that are disclosed further in the detailed description of the embodiments. This summary is not intended to identify key or essential inventive concepts of the claimed subject matter, nor is it intended for determining the scope of the claimed subject matter.

The embodiments described herein generally relate to a rare-earth-free (RE-free) alloy, including material characteristics and corrosion resistance for specific biomedical applications requiring different corrosion rates including, for example, faster degradation for larger orthopedic applications, medium degradation for micro fixation applications, or slow degradation for smaller form applications such as stents.

The embodiments described herein generally relate to an improved magnesium RE-free alloy characterized by an initial stage (Stage I) of absorption slow enough to avoid or minimize a negative biological response, a second "plateau" stage (Stage II) that lasts beyond healing to maintain adequate strength of the device through its useful life, and a third stage (Stage III) including an accelerating absorption rate, that does not negatively impact healing, which occurs after the useful life of a temporary implant device.

The embodiments described herein generally relate to an improved magnesium RE-free alloy which may be a zinc, calcium, manganese (ZXM), magnesium alloy with indication specific absorption profile characteristics.

The embodiments described herein generally relate to a magnesium alloy including about 2-4% by weight zinc;

about 1-2% by weight calcium; about 0-1.0% by weight of an alloying element; and a balance of magnesium.

The embodiments described herein generally relate to a magnesium alloy including about 3-7% by weight zinc; about 0.5-3% by weight calcium; about 0-1.0% by weight of an alloying element; and a balance of magnesium.

The embodiments described herein generally relate to a product including a magnesium alloy comprising: about 3-7% by weight zinc; about 0.5-3% by weight calcium; about 0-1.0% by weight of an alloying element; and a balance of magnesium.

BRIEF DESCRIPTION OF THE DRAWINGS

A complete understanding of the present embodiments and the advantages and features thereof will be more readily understood by reference to the following detailed description when considered in conjunction with the accompanying drawings wherein:

Some embodiments of the present invention are illustrated as an example and are not limited by the elements of the accompanying drawing, in which like references may indicate similar elements and in which:

FIG. 1 depicts an illustrative absorption profile of one variation of the disclosed alloy with a ternary absorption profile.

The drawings are not necessarily to scale, and certain features and certain views of the drawings may be shown exaggerated in scale or in schematic in the interest of clarity and conciseness.

DETAILED DESCRIPTION OF THE INVENTION

The specific details of the single embodiment or variety of embodiments described herein are to the described composition. Any specific details of the embodiments are used for demonstration purposes only, and no unnecessary limitations or inferences are to be understood therefrom.

Before describing exemplary embodiments in detail, it is noted that the embodiments reside primarily in combinations of components and procedures related to the disclosed composition. Accordingly, the composition components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

The specific details of a single embodiment or a variety of embodiments described herein are set forth in this application. Any specific details of the embodiments are used for demonstration purposes only, and no unnecessary limitation or inferences are to be understood therefrom. Furthermore, as used herein, relational terms, such as "first" and "second," "top" and "bottom," and the like, may be used to distinguish one entity or element from another entity or element without necessarily requiring or implying any physical or logical relationship, or order between such entities or elements.

In use, temporary implants need to maintain mechanical support and integrity until healing within an implant recipient is achieved and temporary implant is no longer needed. In general, a relatively slower absorption rate during healing may accelerate to a higher absorption rate after healing such that the entire implant may be gone after one to two years. Such an absorption profile may be achieved by using larger volume fractions of zinc (Zn) and calcium (Ca) (1% by weight or higher) and by adjusting the Zn to Ca ratio in a magnesium-calcium-zinc (Mg—Ca—Zn) based alloy system. The disclosed RE-free magnesium alloy may reduce biocompatibility issues associated with RE alloying by limiting alloying elements to Ca, Zn, and in some embodiments Mn.

The absorption profile may be further modified by using a third alloying element, such as manganese (Mn). Increasing Mn content may increase the formation of a more stable surface oxide which slows corrosion and prolongs the life of an implant to fit the exact needs of the implant's functional life. The third alloying element may also be aluminum (Al) or strontium (Sr).

The present disclosure generally relates to an RE-free magnesium alloy including about 2-4% by weight Zn, about Alternatively, an RE-free magnesium alloy may include about 2-5% by weight Zn, about 1-3% by weight Ca, about 0-1% by weight Mn (or some other alloying element) and the balance magnesium (and inevitable impurities).

Alternatively, an RE-free magnesium alloy may include about 2-5% by weight Zn, about 0.35-1% by weight Ca, about 0-1% by weight Mn (or some other alloying element) and the balance magnesium (and inevitable impurities).

Alternatively, an RE-free magnesium alloy may include about 1.4-4.0% by weight Zn, about 0.2-1% by weight Ca, about 0-1% by weight Mn (or some other alloying element) and the balance magnesium (and inevitable impurities).

According to some embodiments, the disclosed RE-free magnesium alloy may include alloying elements and trace elements, by weight percent, as shown in Table 1:

TABLE 1

| Alloy | Mg | Alloying Elements | | | Trace Elements | | | | |
|---|---|---|---|---|---|---|---|---|---|
| | | Zn | Ca | Mn | Fe | Ni | Cu | Al | Si |
| A1 | balance | 2.0 ± 0.2 | 1.0 ± 0.2 | 0.6 ± 0.2 | <0.010 | <0.010 | <0.010 | <0.010 | <0.010 |
| A2 | balance | 2.0 ± 0.2 | 1.0 ± 0.2 | 0.4 ± 0.2 | <0.010 | <0.010 | <0.010 | <0.010 | <0.010 |
| A3 | balance | 2.5 ± 0.2 | 1.0 ± 0.2 | 0.6 ± 0.2 | <0.010 | <0.010 | <0.010 | <0.010 | <0.010 |
| A4 | balance | 2.5 ± 0.2 | 1.0 ± 0.2 | 0.4 ± 0.2 | <0.010 | <0.010 | <0.010 | <0.010 | <0.010 |
| A5 | balance | 2.5 ± 0.2 | 1.0 ± 0.2 | 0.2 ± 0.2 | <0.010 | <0.010 | <0.010 | <0.010 | <0.010 |
| A6 | balance | 3.0 ± 0.2 | 1.0 ± 0.2 | 0.4 ± 0.2 | <0.010 | <0.010 | <0.010 | <0.010 | <0.010 |
| A7 | balance | 3.0 ± 0.2 | 1.0 ± 0.2 | 0.2 ± 0.2 | <0.010 | <0.010 | <0.010 | <0.010 | <0.010 |
| A8 | balance | 3.5 ± 0.2 | 1.0 ± 0.2 | 0.2 ± 0.2 | <0.010 | <0.010 | <0.010 | <0.010 | <0.010 |

1-2% by weight Ca, about 0-1.0% by weight Mn, or some other alloying element, and the balance of magnesium (and inevitable impurities).

The microstructure of the magnesium alloy may include an $\alpha$-Mg phase matrix and nanometric intermetallic particles (IMPs). The IMPs may be dispersed and precipitated in the form of particles in the magnesium matrix and made of a composition of binary $Mg_2Ca$, which may be anodic to the magnesium matrix. The $\alpha$-Mg phase matrix may also contain monolayer ordered structures consisting of Mg and other alloying elements, including Zn and Ca, situated on the basal (0001) plane of the $\alpha$-Mg matrix, known as Guinier-Preston (GP) zones.

Alternatively or simultaneously, the IMPs may be ternary phase IMPs, such as $Ca_2Mg_6Zn_3$ (IM1), dispersed and precipitated in the form of particles in the magnesium matrix and which may be cathodic to the magnesium matrix. The ratio of binary $Mg_2Ca$ phase and IM1 phase may be optimized to meet a specific application's absorption requirements by the Zn to Ca ratio, where a higher Zn:Ca ratio may produce more ternary IM1 phase and a smaller Zn:Ca ratio may produce more $Mg_2Ca$ phase.

The Zn:Ca ratio may be modified within different alloy compositions to further modify the absorption profile. Other compositional variations of the disclosed magnesium alloy may include the following:

An RE-free magnesium alloy may include about 3-7% by weight Zn, about 0.5-3% by weight Ca, about 0-1% by weight Mn, (or some other alloying element), and the balance magnesium (and inevitable impurities).

The disclosed magnesium alloys may have mechanical properties that are affected by both alloy composition and thermomechanical processing. Thermomechanical processing of the disclosed alloy systems may be optimized by introducing grain boundary pinning (GBP) via secondary phases such as $Mg_2Ca$ and $\alpha$-Mn. Increasing GBP may increase the strength and ductility of the disclosed magnesium alloys.

According to one embodiment, an extrusion temperature of the disclosed magnesium alloys may be modified to alter the volume fraction of secondary phases in the matrix. The volume fraction may be further manipulated by annealing phases into solution at temperatures above 400° C., in some embodiments this step may occur before, and in some embodiments after, a hot or cold deformation process such as extrusion, hot-rolling, equal channel angular pressing, hot drawing, cold drawing, annealing, or any combination thereof.

The disclosed magnesium allows may be modified by precipitating additional secondary phase by aging at lower temperatures or modifying the Zn:Ca ratio. Aging effects may be further improved by adding hot or cold deformation process(es) to the alloy, which may produce dislocations where additional precipitates and Guinier—Preston (GP) zones may nucleate in greater volume fraction and/or density. Aging may be performed at temperatures between 150° C. and 250° C. Some deformation processing has the added benefit of grain refinement, increasing grain boundary area where solute elements, such as Zn and Ca, may segregate at the expense of forming secondary phases, primarily the IM1 and other ternary phases, during aging. In some embodiments, suppressing formation and/or growth of ternary phases through solution treating and/or ageing decreases the slope and time of Stage I while increasing the time of Stage III absorption to extend implant life. Alternatively, in other embodiments, aging at temperatures between 350° C. and 400° C. causes formation and growth of ternary phases through elimination of GP zones and grain boundary solute elements, increasing the slope of Stage I and Stage III to reduce implant life.

The disclosed magnesium alloys may be formed, such as via casting, in an inert atmosphere, such as SF6 or Argon. Formed magnesium alloys may be solution treated at a minimum temperature of approximately 400° C. for approximately one hour to increase ease of manufacture by reducing material variations producing more stable process results, for example, extrusion pressure, speed, and temperature. The solution treatment may achieve more uniform and predictable mechanical, absorption, and microstructural properties. Following solution treatment, the billet may be extruded and drawn, such as via deformation processing, to achieve final raw material shape and material properties.

Additionally, deformation processing and/or heat treatment may be performed at a temperature ranging from about 200° C. to about 400° C. Deformation processing and heat treating under 400° C. may facilitate the formation of both binary $Mg_2Ca$ phase, IM1 phase, and GP Zones. Temperatures from about 350° C. to about 400° C. may be used to increase the volume fraction of IM1 phase through elimination of GP zones to increase the slopes of Stage I and Stage III absorption. Alternatively, utilizing process temperatures in the range of about 200° C. to about 350° C. will suppress IM1 formation thus lowering the slopes of Stage I and III absorption.

FIG. 1 depicts an illustrative absorption profile 100 of one variation of an RE-free magnesium alloy including a ternary absorption profile, wherein the absorption rate may start at a first rate 102 in Stage I, slow to a lower second rate 104 in Stage II relative to the first stage as a protective oxide layer forms on the surface of the implant, (such that the percentage of implant absorbed plateaus or nearly plateaus) and accelerate to a substantially faster third rate 106 in Stage III, which may be faster that the second rate 104 in Stage II, as the protective surface oxide layer becomes destabilized and breaks down. According to some embodiments, the first absorption rate and third absorption rate may be approximately equal. According to some embodiments, the third absorption rate may be faster than the first absorption rate. Healing 108 may be achieved approximately during Stage I or Stage II, and most often during Stage II.

The timescales and rates within each stage may be increased or decreased depending on the alloy composition (e.g., Zn:Ca ratio, alloying elements wt. %) and alloy processing (e.g., extrusion temperatures, extrusion ratios, extrusion rates, aging times and temperatures, solution treatment times and temperatures).

According to one embodiment, full healing near the location of implantation (e.g., healed osteotomy, healed artery) may be achieved during Stage II. In other embodiments, full healing may be achieved during Stage I. The ternary absorption profile may be achieved through alloying the magnesium with Zn, Ca, and, in some embodiments, Mn, thus taking advantage of Mn alloying to form a protective oxide layer more immediately post-implantation and stabilize the oxide layer during Stage II of absorption through healing. Additional alloying elements, such as but not limited to, Zinc, Nickel, Iron, Sodium, Silver, or Tin, may be utilized to facilitate destabilization of the oxide layer post-healing to accelerate absorption rate in a third stage. Modifying the weight percentage of Zn or Ca, and therefore the Zn:Ca ratio, the ratio of $Mg_2Ca$ to IM1 phase may also be adjusted. Adjusting the $Mg_2Ca$ to IM1 phase may adjust the absorption profile; where an increase in Zn:Ca may increase the percentage of IM1 phase and therefor increase the absorption rate of the alloy. Alternatively, decreasing the weight percentage of Zn may increase the percentage of $Mg_2Ca$ phase and decrease the overall absorption rate of an alloy. In addition, by adjusting the ratio of $Mg_2Ca$ to IM1 phase in the Mg alloy, the transition from Stage II to Stage III of the absorption profile may be modified to meet the needs of a specific application. The absorption profile may further be modified by varying the amount of Mn present in the alloy, where increases in Mn prolong the time to enter Stage III, which acts to stabilize the protective oxide layer on the surface of the implant to slow absorption. Increased Mn may stabilize the oxide layer and prevent the penetration of destabilizing chlorine and other ions which facilitate corrosion reactions. The absorption profile may further be modified by varying the amount of a third alloying element present to prolong the time in Stage II while slowing the slope between Stage I and Stage II, as well as the slope between Stage II and Stage III.

The additions of Ca and Zn as alloying elements at higher alloy content levels (1 wt. % or higher) within a solution treatment step may allow for manipulating the formation of the desired precipitate phases ($Mg_2Ca$ and IM1 phase) with an overall increased volume fraction of phases. This approach encourages breakdown of the protective surface oxide layer, allowing faster absorption at later stages (after healing), such as during the Stage III. The addition of manganese may facilitate controlling the absorption rate in the early stages of implantation. The addition of manganese may also facilitate refinement of grain size and therefor improve the strength and ductility of the alloy.

According to some embodiments, the disclosed RE-free magnesium alloy may include tensile properties as shown in Table 2:

TABLE 2

| Alloy | Avg YS$_{-0.2\%}$ (MPa) | Avg UTS (MPa) | Avg % Elong. (%) |
|---|---|---|---|
| A1 | 292 | 310 | 7.2 |
| A2 | 265 | 301 | 11.5 |
| A3 | 292 | 317 | 9.7 |
| A4 | 292 | 319 | 9.0 |
| A5 | 287 | 313 | 8.5 |
| A6 | 286 | 311 | 8.5 |
| A7 | 261 | 298 | 11.3 |
| A8 | 293 | 321 | 8.7 |

According to some embodiments, the absorption rate of the alloy when immersed in Dulbecco's Modified Eagle's Medium (DMEM) at 37° C. under a 5% carbon-dioxide environment may not exceed 0.2 mm/yr. prior to Stage III absorption. In other embodiments the absorption rate may not exceed 0.1 mm/yr. prior to Stage III absorption. In some embodiments the transition to Stage III absorption occurs after 500 hours, in others 1000 hours, and other 1500 hours.

According to some embodiments the alloy may be processed using a deformation step in the range of about 200° C. to about 400° C. followed by a heat treatment. In some embodiments, the heat treatment may be performed between about 200° C. to about 350° C. to maximize the life of the implant, and in other embodiments the heat treatment may be performed between about 350° C. to about 400° C. to decrease the life of the implant. In other embodiments, implant life may be decreased by utilizing a deformation process performed in the temperature range of about 350° C. to about 400° C.

The following description of variants is only illustrative of components, elements, acts, product, and methods considered to be within the scope of the invention and are not in any way intended to limit such scope by what is specifically disclosed or not expressly set forth. The components, elements, acts, product, and methods as described herein may be combined and rearranged other than as expressly described herein and still are considered to be within the scope of the invention.

According to variation 1, a magnesium alloy may comprise, consist of, or consist essentially of about 2-4% by weight zinc; about 1-2% by weight calcium; about 0-1.0% by weight of an alloying element; and a balance of magnesium.

Variation 2 may include a magnesium alloy as in variation 1, wherein the alloying element comprises manganese.

Variation 3 may include a magnesium alloy as in variation 1 or 2, wherein the content of manganese is 0.4-1.0% by weight.

Variation 4 may include a magnesium alloy as in any of variations 1 through 3, wherein the content the alloying element is about 0.1-0.5% by weight.

Variation 5 may include a magnesium alloy as in any of variations 1 through 4, wherein the content of each impurity is less than 0.1% by weight.

Variation 6 may include a magnesium alloy as in any of variations 1 through 5, wherein the magnesium alloy is free from rare-earth elements.

According to variation 7, a magnesium alloy may comprise, consist of, or consist essentially of about 3-7% by weight zinc; about 0.5-3% by weight calcium; about 0-1.0% by weight of an alloying element; and a balance of magnesium.

Variation 8 may include a magnesium alloy as in variation 7, wherein the alloying element comprises manganese.

Variation 9 may include a magnesium alloy as in variations 7 or 8, comprising about 2-5% by weight zinc.

Variation 10 may include a magnesium alloy as in any of variations 7 through 9, comprising about 1.4-4% by weight zinc.

Variation 11 may include a magnesium alloy as in any of variations 7 through 10, comprising about 1-3% by weight calcium.

Variation 12 may include a magnesium alloy as in any of variations 7 through 11, comprising about 0.35-1% by weight calcium.

Variation 13 may include a magnesium alloy as in any of variations 7 through 12, comprising about 0.2-1% by weight calcium.

Variation 14 may include a magnesium alloy as in any of variations 7 through 13, comprising a ternary absorption profile comprising a first stage, second stage, and third stage.

Variation 15 may include a magnesium alloy as in any of variations 7 through 14, wherein the first stage comprises a first absorption rate.

Variation 16 may include a magnesium alloy as in any of variations 7 through 15, wherein the second stage comprises a second absorption rate.

Variation 17 may include a magnesium alloy as in any of variations 7 through 16, wherein the third stage comprises a third absorption rate.

Variation 18 may include a magnesium alloy as in any of variations 7 through 17, wherein the first absorption rate is approximately faster than the second absorption rate and wherein the third absorption rate is approximately faster than the second absorption rate.

According to variation 19, a product may include a magnesium alloy including about 2-7% by weight zinc; about 0.2-3% by weight calcium; about 0-1.0% by weight of an alloying element; and a balance of magnesium.

Variation 20 may include a product as in variation 19, wherein the product is an implant.

In this disclosure, the descriptions of the various embodiments have been presented for purposes of illustration and are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein. Thus, the appended claims should be construed broadly, to include other variants and embodiments, which may be made by those skilled in the art.

We claim:

1. A magnesium alloy comprising:
zinc in an amount within a range from greater than 2 wt. % to about 4 wt. %;
calcium in an amount within a range from about 1 wt. % to about 2 wt. %, wherein a ratio of zinc to calcium is between 2.5:1 and 3.0:1;
manganese in an amount within a range from about 0.7 wt. % to about 1.0 wt. %;
and a balance of magnesium,
wherein a microstructure of the magnesium alloy comprises an a-Mg phase matrix and nanometric intermetallic particles,
wherein the nanometric intermetallic particles comprise:
a binary phase $Mg_2Ca$; and
a ternary phase of $Ca_2Mg_6Zn_3$ dispersed in the $\alpha$-Mg phase matrix, and
wherein the microstructure provides an absorption rate of the alloy of less than 0.2 millimeters per year for a duration not less than 500 hours.

2. The magnesium alloy of claim 1, wherein a content of each impurity is present in an amount of less than about 0.1% by weight.

3. The magnesium alloy of claim 1, wherein the magnesium alloy excludes rare-earth elements as alloying additions.

4. A magnesium alloy comprising:
zinc in an amount within a range from about 1.4 wt. % to about 7.0 wt. %;
calcium in an amount within a range from about 0.5 wt. % to about 3 wt. %, wherein a ratio of zinc to calcium is between 2.5:1 and 3.0:1;
manganese in an amount within a range from about 0.7 wt. % to about 1.0 wt. %; and
a balance of magnesium,
wherein a microstructure of the magnesium alloy comprises nanometric intermetallic particles including $Mg_2Ca$ and $Ca_2Mg_6Zn_3$ dispersed in an $\alpha$-Mg phase matrix, and
wherein the microstructure provides an absorption rate of the alloy of less than 0.1 millimeters per year for a duration not less than 500 hours.

5. The magnesium alloy of claim 4, wherein the absorption rate is defined by a ternary absorption profile comprising a first stage, second stage, and third stage.

6. The magnesium alloy of claim 5, wherein the first stage comprises a first absorption rate.

7. The magnesium alloy of claim 6, wherein the second stage comprises a second absorption rate.

8. The magnesium alloy of claim 7, wherein the third stage comprises a third absorption rate.

9. The magnesium alloy of claim 8, wherein the first absorption rate is approximately faster than the second absorption rate and wherein the third absorption rate is approximately faster than the second absorption rate.

10. A product comprising:

a magnesium alloy comprising:

zinc in an amount within a range from about 1.4 wt. % to about 7.0 wt. %;

calcium, wherein a ratio of zinc to calcium is between 2.5:1 and 3.0:1;

manganese in an amount within a range from about 0.7 wt. % to about 1.0 wt. %; and a balance of magnesium, wherein a microstructure of the magnesium alloy comprises nanometric intermetallic particles including $Mg_2Ca$ and $Ca_2Mg_6Zn_3$ dispersed in an $\alpha$-Mg phase matrix, and wherein the microstructure provides an absorption rate of the alloy of less than 0.1 millimeters per year for a duration not less than 500 hours.

11. A product as in claim 10, wherein the product is an implant.

* * * * *